US012582361B2

(12) United States Patent
Jha et al.

(10) Patent No.: US 12,582,361 B2
(45) Date of Patent: Mar. 24, 2026

(54) SYSTEMS AND METHODS FOR LOW-COUNT QUANTITATIVE PROJECTION DOMAIN SPECT IMAGING

(71) Applicant: Washington University, St. Louis, MO (US)

(72) Inventors: Abhinav Kumar Jha, St. Louis, MO (US); Zekun Li, St. Louis, MO (US); Daniel Thorek, St. Louis, MO (US); Md Ashequr Rahman, St. Louis, MO (US)

(73) Assignee: Washington University, St. Louis, MO (US)

( * ) Notice: Subject to any disclaimer, the term of this patent is extended or adjusted under 35 U.S.C. 154(b) by 165 days.

(21) Appl. No.: 18/578,227

(22) PCT Filed: Jul. 13, 2022

(86) PCT No.: PCT/US2022/036921

§ 371 (c)(1),
(2) Date: Jan. 10, 2024

(87) PCT Pub. No.: WO2023/287857

PCT Pub. Date: Jan. 19, 2023

(65) Prior Publication Data

US 2024/0307008 A1     Sep. 19, 2024

Related U.S. Application Data

(60) Provisional application No. 63/221,913, filed on Jul. 14, 2021.

(51) Int. Cl.
*A61B 6/03* (2006.01)
*A61B 6/00* (2024.01)
(Continued)

(52) U.S. Cl.
CPC .............. *A61B 6/032* (2013.01); *A61B 6/469* (2013.01); *A61B 6/5258* (2013.01); *G06F 30/25* (2020.01)

(58) Field of Classification Search
CPC ....... A61B 6/037; A61B 6/469; A61B 6/5258; A61B 6/032; A61B 6/5205; A61B 6/5229;
(Continued)

(56) References Cited

U.S. PATENT DOCUMENTS 10,973,486 B2     4/2021   Sjoestrand et al.
2021/0073950 A1   3/2021   Vija et al.
(Continued)

FOREIGN PATENT DOCUMENTS

WO     2008025941 A1     3/2008
WO     2021084087 A1     5/2021

OTHER PUBLICATIONS

International Search Report and Written Opinion issued for International Application No. PCT/US2022/36921, dated Oct. 17, 2022 (10 pages).

*Primary Examiner* — Irakli Kiknadze
(74) *Attorney, Agent, or Firm* — ARMSTRONG TEASDALE, LLP

(57) ABSTRACT

A system for low-count quantitative single-photon emission computed tomography (LC-QSPECT) is provided. The system is programmed to a) store a computer tomography (CT) scan of a subject being examining including a plurality of defined volumes of interest (VOIs) of the subject being examined; b) model a system matrix based on the stored CT, wherein the model describes the probability that photons emitted from each of the defined VOIs are detected in different projection bins, wherein a plurality of projection bins are defined around the subject and the defined VOIs; c) adjust the model with analysis of stray-radiation noise
(Continued)

around the subject; d) detect, by the one or more sensors, one or more photons being emitted by an alpha-particle-emitting isotope; and e) execute the adjusted model with the one or more detected photons as inputs to determine a source VOI of the detected photons.

20 Claims, 5 Drawing Sheets

(51) Int. Cl.
  *A61B 6/46*          (2024.01)
  *G06F 30/25*         (2020.01)
(58) Field of Classification Search
  CPC ....... A61B 6/4417; A61B 6/54; A61B 6/4435; A61B 6/107; A61B 6/5264; A61B 6/5282; A61B 6/4258; A61B 6/4266; A61B 6/0407; A61B 6/0487; A61B 6/4275; A61B 6/4291; A61B 6/5235; A61B 6/507; A61B 6/504; A61B 6/503; A61B 6/483; A61B 6/5247; A61B 6/481; A61B 6/5217; A61B 5/055; A61B 6/5294; A61B 6/03; A61B 6/488; A61B 6/5211; A61B 6/541; A61B 6/542; A61B 6/545; A61B 6/56; A61B 6/4085; A61B 6/4078; A61B 6/46; G06F 30/25; G06F 3/04842; G01T 1/1647; G01T 1/1611; G01T 1/1644; G01T 1/249; G01T 7/00; G01T 1/1642; G01T 1/1648; G01T 1/1641; G06T 11/005; G06T 11/006; G06T 2211/424; G06T 2210/41; G06T 2207/30004; G06T 2207/10108; G06T 2211/412; G06T 5/60; G06T 7/0012; G06T 5/70; G06T 2207/20081; G06T 2211/441; G06T 7/33; G06T 7/38; G06T 2207/10104; G06T 2207/10081; G06T 2207/30008; G06T 2207/30061; G06T 11/008; G06T 11/003; G06T 5/50; G06T 2207/10072; G06T 2207/20224; G06T 2211/464; G06T 2207/30024; G06T 2207/10088; G06T 2211/432; G06T 15/00; G06T 2207/30096; G06T 2207/30081; G06T 19/20; G06T 2207/20076; G06T 2207/20084; G06V 10/26; G06V 2201/031; G06V 10/25; G06V 10/40; G06V 10/70; G06V 2201/03; G06V 10/82; A61N 5/1071; A61N 2005/1087; G21K 1/025; G21K 1/02; G16H 50/30; G16H 50/20; G16H 30/40; G16H 30/20; G16H 10/60; G16H 50/70; G06N 3/0455; G06N 3/0464; G06N 3/0475; G06N 3/045; G06N 20/00; G06N 3/0495; G06N 3/08; G06N 3/09; H02J 9/061; H02J 9/062; H02J 3/36; A61K 31/198; A61K 47/20; A61K 47/22; A61K 51/0446; A61K 51/0497; A61K 47/02; A61K 31/69; A61K 47/12; A61K 38/05; A61K 2300/00; A61P 35/00
  USPC .................................................. 378/4, 19, 62
  See application file for complete search history.

(56)              References Cited

U.S. PATENT DOCUMENTS

| | | | |
|---|---|---|---|
| 2021/0093249 A1* | 4/2021 | Anand ................... | G06N 20/00 |
| 2021/0334974 A1* | 10/2021 | Johnsson ................. | G06T 7/11 |
| 2022/0005586 A1* | 1/2022 | Brynolfsson .......... | G16H 30/40 |
| 2022/0031273 A1* | 2/2022 | Lewis ................... | A61B 6/527 |
| 2022/0117570 A1* | 4/2022 | Profio ................... | A61B 6/481 |
| 2022/0284643 A1* | 9/2022 | Jha ........................ | G06T 11/005 |

* cited by examiner

SYSTEMS AND METHODS FOR LOW-COUNT QUANTITATIVE PROJECTION DOMAIN SPECT IMAGING

CROSS REFERENCE TO RELATED APPLICATIONS

This application is a U.S. National Stage Entry of International Patent Application No. PCT/US2022/036921, filed Jul. 13, 2022, which claims the benefit of and priority to U.S. Provisional Patent Application No. 63/221,913, filed Jul. 14, 2021, which are hereby incorporated by reference in their entireties.

STATEMENT REGARDING FEDERALLY SPONSORED RESEARCH & DEVELOPMENT

This invention was made with government support under EB024647 awarded by the National Institutes of Health. The government has certain rights in the invention.

BACKGROUND OF THE DISCLOSURE

The present disclosure generally relates to computer-aided systems and methods of performing low-count quantitative SPECT imaging, and more specifically to performing low-count quantitative SPECT imaging in combination with radiopharmaceutical therapy.

Alpha particle-emitting radiopharmaceutical therapies (αRPTs) are an emerging class of highly cytotoxic therapies that are highly effective for targeted cancer therapies and are gaining increasing clinical significance, particularly in treating patients with late-stage metastatic disease. Systemically administered αRPTs have the capability to localize to disease sites throughout the patient to kill cancer cells resistant to conventional therapies. However current αRPT paradigms are not personalized, and administered activity is dependent merely on mass, leading to non-optimal therapies.

There is an important need for methods to estimate the dose that these therapies provide, and quantifying the uptake with these isotopes using SPECT provides a way to perform this estimation. This is challenging due to the low numbers of detected counts when imaging these agents (20 times lower than conventional SPECT imaging studies). Further, the spectra of these radio-isotopes are very complicated. As a result, the conventional methods yield inaccurate and imprecise performance.

Quantifying the absorbed dose to both sites of disease and at-risk organs is crucial for adapting treatment regimens, and for the prediction of therapy outcomes and adverse events. Quantitative SPECT provides an excellent translatable mechanism to perform this quantification. However, this is challenging in αRPT due to the ultra-low photon counts (up to 3 orders of magnitude lower than in diagnostic SPECT). Existing SPECT quantification protocols are erroneous at such low counts and personalized administration cannot be performed. Thus, there is an urgent need for radically new methods for quantitative SPECT for αRPTs.

BRIEF DESCRIPTION

In a first aspect, a system for low-count quantitative single-photon emission computed tomography (LC-QSPECT) is provided. The system includes one or more sensors configured for detecting one or more emitted photons. The system also includes a computer device in communication with the one or more sensors. The computer device comprises at least one processor in communication with at least one memory device. The at least one processor is programmed to store a computer tomography (CT) scan of a subject being examining including a plurality of defined volumes of interest (VOIs) of the subject being examined. The at least one processor is also programmed to model a system matrix based on the stored CT scan, wherein the model describes the probability that photons emitted from each of the defined VOIs are detected in different projection bins. A plurality of projection bins are defined around the subject and the defined VOIs. The at least one processor is further programmed to adjust the model with analysis of stray-radiation noise around the subject. In addition, the at least one processor is programmed to detect, by the one or more sensors, one or more photons being emitted by an alpha-particle-emitting isotope. Furthermore, the at least one processor is programmed to execute the adjusted model with the one or more detected photons as inputs to determine a source VOI of the detected photons. The system may include additional, less, or alternate functionality, including that discussed elsewhere herein.

In a second aspect, a method for low-count quantitative single-photon emission computed tomography (LC-QSPECT) is provided. The method is implemented by a computer device comprising at least one processor in communication with one or more memory devices and in communication with one or more sensors configured for detecting one or more emitted photons. The method includes storing a computer tomography (CT) scan of a subject being examining including a plurality of defined volumes of interest (VOIs) of the subject being examined. The method also includes modeling a system matrix based on the stored CT scan, wherein the model describes the probability that photons emitted from each of the defined VOIs are detected in different projection bins. A plurality of projection bins are defined around the subject and the defined VOIs. The method further includes adjusting the model with analysis of stray-radiation noise around the subject. In addition, the method includes detecting, by the one or more sensors, one or more photons being emitted by an alpha-particle-emitting isotope. Furthermore, the method includes executing the adjusted model with the one or more detected photons as inputs to determine a source VOI of the detected photons. The method may include additional, less, or alternate functionality, including that discussed elsewhere herein.

In a third aspect, a computer device for low-count quantitative single-photon emission computed tomography (LC-QSPECT) is provided. The computer device includes at least one processor in communication with at least one memory device. The at least one processor is programmed to store a computer tomography (CT) scan of a subject being examining including a plurality of defined volumes of interest (VOIs) of the subject being examined. The at least one processor is also programmed to model a system matrix based on the stored CT scan, wherein the model describes the probability that photons emitted from each of the defined VOIs are detected in different projection bins. A plurality of projection bins are defined around the subject and the defined VOIs. The at least one processor is further programmed to adjust the model with analysis of stray-radiation noise around the subject. In addition, the at least one processor is programmed to detect, by one or more sensors, one or more photons being emitted by an alpha-particle-emitting isotope within the subject. Furthermore, the at least one processor is programmed to execute the adjusted model with the one or more detected photons as inputs to determine a source VOI of the detected photons. The computer device may include additional, less, or alternate functionality, including that discussed elsewhere herein.

BRIEF DESCRIPTION OF THE DRAWINGS

Those of skill in the art will understand that the drawings, described below, are for illustrative purposes only. The drawings are not intended to limit the scope of the present teachings in any way.

Figure 1:
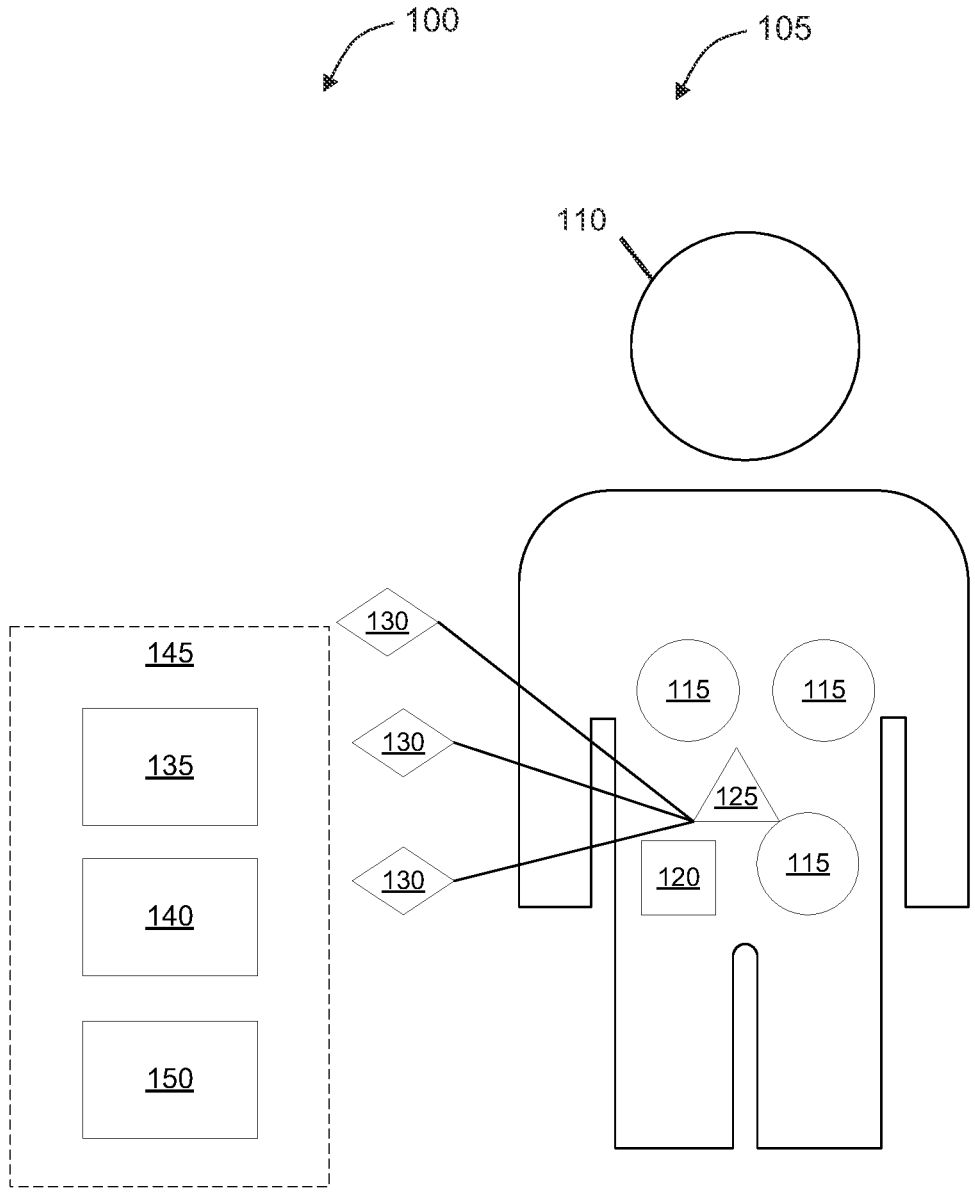
FIG. 1 illustrates a system for performing low-count quantitative SPECT imaging in a radiopharmaceutical therapy environment in accordance with at least one embodiment.

There are shown in the drawings arrangements that are presently discussed, it being understood, however, that the present embodiments are not limited to the precise arrangements and are instrumentalities shown. While multiple embodiments are disclosed, still other embodiments of the present disclosure will become apparent to those skilled in the art from the following detailed description, which shows and describes illustrative aspects of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

In various aspects, devices and methods of performing low-count quantitative SPECT imaging. In one aspect, a quantitative SPECT-based method to measure and identify the source of low-levels of radiation is discussed. In at least one aspect, the low-count SPECT imaging is used in a radiopharmaceutical therapy environment. The radiopharmaceutical therapy may include targeted radionuclide therapy with α-particle-emitting therapeutic isotopes. These may include, but are not limited to, therapies based on Radium-223, Actinium-225, Bismuth-213, Astatine-211, Thorium-227, Iodine-131, HM-90, and other therapeutic tracers. These targeted therapies are applied to tumors to ablate said tumors while minimizing the damage to the surrounding normal tissues. These isotopes distribute throughout the patient, accumulating to unknown levels at sites of disease and in radiosensitive vital organs. Thus, methods to quantify absorbed doses in lesions and at-risk organs are much needed to adapt treatment regimens, predict therapy outcomes, and monitor adverse events.

Often, the α-particle-emitting isotopes also emit γ-ray photons that can be detected by a γ camera. This provides a mechanism to quantify the absorbed dose from the regional activity uptake in organs and lesions. In at least one aspect, single-photon emission computed tomography (SPECT)-based methods are used to detect those γ-ray photons and detect their point of origin in the body. Conventional SPECT algorithms require updating as described herein to correct for background radiation activity. Conventional analysis methods are challenged at low number of detected counts, as is the case in alpha particle-emitting radiopharmaceutical therapies (α-RPTS), where the administered activity is up to 1000 times lower than SPECT with conventional radionuclide therapies. For example, when imaging with Radium-223, the number of detected counts can be as low as 5,000 counts per axial slice in the projection domain.

In at least one aspect, the SPECT system is used to detect the absorbed dose in organs and tumors for α-RPTs. In some further aspects, the disclosed quantitative SPECT methods use data from multiple energy windows directly for quantification of the tracer uptake.

Existing quantitative SPECT methods use only limited data from a single energy window and perform image reconstruction (measuring activity in all the voxels) before performing quantification. In the case of alpha particle-emitting radiopharmaceutical therapies (αRPTs), relatively low numbers of particles are emitted, posing a challenge for existing quantitative SPECT methods due to the relative scarcity of data. To address the low-count issue, the disclosed method enhances the amount of data available for analysis by using data from multiple energy windows for quantification. In various aspects, the disclosed quantitative SPECT method makes use of data corresponding to different photopeaks of the spectra, as well as scatter-window data. In addition, the disclosed quantitative SPECT method estimates activity in the different organs directly from projection data, rather than estimating all the voxel uptake by reconstruction, as is performed in existing quantitative SPECT methods, theoretically making the quantification task more well-posed.

In at least one aspect, the methods described herein describe a low-count quantitative SPECT (LC-QSPECT) method that uses direct quantification from projection data while incorporating the modeling of stray-radiation-related noise and the imaging physics and spectra of α-RPT isotopes.

In some aspects, different methods of quantifying tracer uptake for α-RPTs are disclosed. Tracers can include, but are not limited to, Radium-223, Actinium-225, and Thorium-227. Other materials may be used with the systems and methods described herein. Since these isotopes distribute throughout the body, including radio-sensitive vital organs, there is an important need to quantify the dose distribution of these isotopes. The disclosed quantitative SPECT methods may be used with post-therapy management, therapy outcomes prediction, and adverse events monitoring.

In various aspects, the projection-domain quantification (PDQ) method is disclosed that determines activities of a plurality of volumes of interest (VOIs) directly from the measured projection data. The PDQ method makes use of a system matrix $H_{mk}$ that describes the probability that photons emitted from $k^{th}$ VOI are detected in the $m^{th}$ projection bin. In various aspects, the system matrix $H_{mk}$ models the physics of the SPECT imaging system. In some aspects, the elements of $H_{mk}$ are obtained using Monte Carlo (MC)-based modeling of the photon propagation as they are emitted from a VOI and reach the detector surface.

By way of non-limiting example, a PDQ computer system models of the physics of the imaging process to generate the elements of the system matrix. In the simulation, the PDQ computer system masks each VOI with unit tracer uptake. The PDQ computer system generates models based on past detected attenuation maps and system masks. The PDQ computer system can also simulate a large number of photons, selectively generating noiseless projection data, which then serves as the corresponding column of the system matrix for each VOI. The effects of attenuation, scatter and collimator detector response (CDR) were all included in the system matrix and simulated.

In various other aspects, the PDQ method makes use of a matrix representing the mean background noise. The noise matrix may be generated by the PDQ computer system by measuring the mean background counts of projection bins of a planar blank scan using the corresponding SPECT system. The computed system matrix and the mean background noise can then be used to solve an iterative equation to estimate the tracer uptake within each VOI directly from the projection data.

In some aspects, the system matrix $H_{mk}$ described above models the physics of the SPECT imaging system to obtain projection data within a single energy window. In another aspect, the system matrix may be expanded by the PDQ computer system to model the physics of the SPECT imaging system to obtain projection data within a plurality of energy windows. The PDQ computer system uses the system matrix to further model cross-talk between the plurality of energy windows.

In an additional aspect, the system matrix described above may also be expanded to model the physics of the SPECT imaging system to obtain projection data from multiple isotopes within a single energy window, including cross-talk between the multiple isotopes and the process of radioactive decay of each isotope. In another additional aspect, the PDQ computer system uses the system matrix described above models the physics of the SPECT imaging system to obtain projection data from multiple isotopes within a plurality of energy windows. In this aspect, the PDQ computer system and the system matrix further models cross-talk between the plurality of energy windows and isotopes as well as the radioactive decay process of the isotopes. In various aspects, the system matrix can be used to model various aspects of the imaging physics including, but not limited to, depth-dependent collimator response, detector response, noise, scatter and absorption within the tissue, energy-dependent septal penetration and scatter, and Pb X-rays.

By way of non-limiting examples, a method of quantitative SPECT using multiple energy windows jointly estimates the regional activity uptake of both $^{227}$Th and $^{223}$Ra directly from SPECT projections. The method is inspired by a dual-isotope SPECT reconstruction approach but performs quantification directly from projections. In this method, the system matrix is defined to account for cross-talk between radionuclides in five different energy windows. A set of coupled equations are derived that relate the measured projections in the different energy windows to the concentration of these isotopes in different VOIs while modeling the cross-talk. These equations also model the $^{227}$Th/$^{223}$Ra decay. The coupled equations are solved iteratively to jointly estimate the regional uptake of the two isotopes.

FIG. 1 illustrates a system 100 for performing low-count quantitative SPECT imaging in a radiopharmaceutical therapy environment 105 in accordance with at least one embodiment.

In the exemplary embodiment, a patient 110 has a plurality of organs 115, where one or more of the organs 115 are radio sensitive. The patient 110 also has one or more tumors 120. The one or more tumors 120 are being treated with an alpha particle-emitting radiopharmaceutical therapy (α-RPT) 125. The α-RPT 125 emits alpha (α) particles, which are absorbed by the surrounding tissue, and gamma (γ)-ray photons 130, which exit the patient's body. A sensor 135, such as, but not limited to, a γ camera, detects the γ-ray photons 130. The sensor 135 is a part of a single-photon emission computed tomography (SPECT) system 140. The SPECT system 140 also includes a projection-domain quantification (PDQ) computer system 145 for performing the calculations described herein to detect the location of the α-RPT 125 based on the detected γ-ray photons 130.

In some embodiments, the SPECT system 140 includes, or is in communication with a computed tomography (CT) device 150. The CT device 150 may be a CT machine or CT scanning machine. The CT device 150 provides scans of the patient, or item being imaged, to allow the SPECT system 140 to determine where on the patient's body the photons originated.

In at least one aspect, a SPECT system 140 imaging a radioisotope distribution f(r), where r=(x, y, z) denotes the spatial 3D coordinates. The measured projection data is denoted by the M-dimensional vector g. The SPECT system 140 assumes that the object being imaged and the projection data lie in the Hilbert space of square-integrable functions, denoted by $L_2(R^3)$ and the Hilbert space of Euclidean vectors, denoted by $E^M$, respectively. Then, the SPECT system 140, denoted by the operator H, is a transformation from $L_2(R^3)$ to $E^M$. In SPECT with α-RPTs 125, the stray-radiation-related noise occupies a substantial portion of the measured counts due to the very low-count levels. The SPECT system 140 models this noise as Poisson distributed with the same mean $\Psi$ for all projection bins. $\Psi$ is an M-dimensional vector with each element equal to $\Psi$ that denotes the mean stray-radiation-related noise across all M projection bins. The entire noise in the imaging system is denoted by the M-dimensional random vector n. Then the SPECT system 140 generates Poisson distributed projection data g with mean $Hf+\Psi$. Thus, the imaging system equation is given by:

$$g = Hf + \Psi + n \qquad \text{EQ. 1}$$

The objective is to estimate the regional uptake within a set of VOIs. Mathematically, the SPECT system 140 first defines a 3D VOI function:

$$\varphi_k^{VOI}(r) = \begin{cases} 1, & \text{if } r \text{ lies within the } k^{th} \text{ VOI} \\ 0, & \text{otherwise} \end{cases} \qquad \text{EQ. 2}$$

λ denotes the K-dimensional vector of regional uptake, where the objective is to estimate λ, where $\lambda_k$ is given by:

$$\lambda_K = \frac{\int d^3 r f(r)\varphi_k^{VOI}(r)}{\int d^3 r \varphi_k^{VOI}(r)} \qquad \text{EQ. 3}$$

In some conventional embodiments, λ is estimated by reconstructing the activity uptake distribute over a voxelized grid, and then estimate the activity uptake in a discretized version of VOI as defined in EQ. 2. However, this procedure to estimate λ has several issues. First, a large number of voxels need to be estimated during reconstruction, leading to a highly ill-posed problem, especially when the number of counts is low, and leads to biased estimates. A second issue is the bias introduced due to partial volume effects (PVEs). PVEs include two distinct phenomena. The first is due to the finite system resolution. Another is the tissue-fraction effects. More specifically, when defining a discretized mask matrix O for the $n^{th}$ voxels as $O_{n,k}$. An element of this matrix is 1 when a majority of this voxel is within the VOI. Therefore, this does not define a continuous VOI, causing bias when estimating $\lambda_k$ from the reconstructed image. The third issue is the activity inside a voxel is fundamentally not estimable. Additionally, by the data-processing inequality, the process of reconstruction can only lead to information loss. Finally, these reconstruction-based quantification (RBQ) approaches are often based on maximum-likelihood expectation maximization (MLEM) or ordered subset expectation maximization (OSEM). However, at low counts, these methods have limited precision and deviate from the theoretically lowest possible Cramér-Rao bound (CRB). All these issues serve as sources of error in the estimated regional activity. Furthermore, even highly fine-tuned versions of these methods yield unreliable estimates of regional uptake.

To address the above-described issues with RBQ methods, the SPECT system's objective is to estimate the mean uptake within certain regions, $\lambda_k$. Thus, the SPECT system 140 directly represents the object f(r) in terms of the VOI-basis functions. These VOI basis functions are given by $\varphi_k^{VOI}(r)$ as defined in EQ. 2. The activity distribution is then represented in terms of these basis functions as:

$$f_{VOI}(r) = \sum_{k=1}^{K} \lambda_k \varphi_k^{VOI}(r) \qquad \text{EQ. 4}$$

where, if the activity inside of each VOI is constant, then $f_{VOI}(r)=f(r)$. Inserting this definition for f(r) in EQ. 1 yields the following expression for the $m^{th}$ element of vector g:

$$g_m = \int h_m(r)f(r)d^3r + \psi + n_m \qquad \text{EQ. 5}$$
$$= \sum_{k=1}^{K} \lambda_k(r)\varphi_k^{VOI}(r)d^3r + \psi + n_m$$

This can be rewritten in vector form as:

$$g = H\lambda + \Psi + n \qquad \text{EQ. 6}$$

where H is the M×K dimensional system matrix with elements given by:

$$H_{mk} = \int d^3r h_m(r)\varphi_k^{VOI}(r) \qquad \text{EQ. 7}$$

Given the measured projection g, to estimate $\lambda$, the SPECT system 140 maximizes the probability of occurrence of the measured data. Next the SPECT system 140 denotes Pr(x) as the probability of a discrete random variable x. Then, the probability of the measured projection data is given by:

$$Pr(g|\lambda) = \prod_{m=1}^{M} Pr(g_m|\lambda) \qquad \text{EQ. 8}$$

where the measured data across the different bins are independent. Now, the measured data $g_m$ is Poisson distributed with mean $(H\lambda)_m+\Psi$. Thus:

$$Pr(g|\lambda) = \prod_{m=1}^{M} \exp[-(H\lambda)_m - \psi]\frac{[(H\lambda)_m + \psi]^{g_m}}{g_m!} \qquad \text{EQ. 9}$$

This gives the likelihood of the measured data g. To estimate $\lambda$, the SPECT system 140 maximizes the logarithm of the likelihood of $\lambda$ given g:

$$\hat{\lambda} = \overset{arg\ max}{\lambda} \ln[Pr(g|\lambda)] \qquad \text{EQ. 10}$$

To maximize this log-likelihood, the SPECT system 140 follows the same process as used to derive the conventional MLEM technique. The SPECT system 140 differentiates the log-likelihood with respect to the elements of $\lambda$ and equate that to 0 to find the point at which the log-likelihood is maximized. This yields the following iterative equation to estimate $\lambda_k$:

$$\hat{\lambda}_k^{(t+1)} = \hat{\lambda}_k^t \frac{1}{\sum_{m=1}^{M} H_{mk}} \sum_{m=1}^{O} \frac{g_m}{\left[H\hat{\lambda}^{(t)}\right]_m + \psi}H_{mk} \qquad \text{EQ. 11}$$

where $\hat{\lambda}_k^t$ denotes the estimate of $\lambda_k$ at the $t^{th}$ iteration. This procedure is the low-count quantitative SPECT (LC-QSPECT) method described herein. This method directly quantifies from projection data by providing the ability to model stray-radiation-related noise. This ability to model stray-radiation-related noise plays a key role in the task of reliable quantification. Further, the system matrix H models all key image-degrading processes in α-particle SPECT using a Monte Carlo (MC)-based approach, which further improves the performance of this technique on the task of reliable quantification.

The LC-QSPECT approach alleviates the issues outlined earlier with RBQ approaches. Typically, the number of VOIs K is less than the number of voxels N. In addition, the method is less sensitive to PVEs since the boundaries of VOIs are defined before estimating the regional uptake. In particular, the tissue-fraction effects are minimized since there is no voxelization. Since the VOI is generally larger than a voxel, the estimation bias is lower. The LC-QSPECT method also directly estimates the regional uptake from the projection data, thus avoiding any reconstruction-related information loss. Finally, the method yields estimates with a precision that is close to the CRB.

Implementing the proposed LC-QSPECT method requires obtaining the elements of the system matrix $H_{mk}$, as shown in EQ. 14. Some of these elements may be obtained using an MC-based approach. More specifically, the SPECT system 140 can be used to model the isotope emission and the system 100 as a whole. Next, for a given patient, the SPECT system 140 obtains the definition of the VOIs. The VOIs can be obtained, for example, by segmenting the CT that is acquired along with the SPECT information. In the exemplary embodiment, a CT scan is provided by the CT device 150. The SPECT system 140 can assign unit uptake to the VOI and zero uptake elsewhere. In some embodiments, the SPECT system 140 generates an attenuation map of the patient based on historical information, either that from the patient or from other historical patients with similar attributes.

Next, the LC-QSPECT method requires obtaining the mean of stray-radiation-related noise, i.e. $\Psi$ in EQ. 11. This can be obtained experimentally from a planar blank scan acquired on the SPECT system 140 for over 10 minutes. Averaging the projection bin counts in this scan yields the mean background counts. This can then be scaled to the acquisition time to estimate the mean stray-radiation-related noise.

The computed system matrix and mean stray-radiation-related noise are used in EQ. 11 to estimate the regional uptake directly from the projection data. As the system matrix modeled all relevant image-degrading processes, these processes were automatically compensated during quantification.

Another important feature of the LC-QSPECT method is the use of an MC simulation-based approach to generate the system matrix. This approach yields highly accurate modeling of SPECT physics. The MC approach is computationally feasible because the number of VOIs is typically quite small. Thus, this matrix can be pre-computed and stored. In clinical applications, the CT scans of the patient are acquired first, then the system matrix can be generated simultaneously when the SPECT scan is acquired. Further, the estimation process is rapid. This is unlike developing such an approach for OSEM-based methods, for which a similar system matrix may require up to 30 TB of memory. Thus, the proposed method provides a mechanism for highly accurate Monte Carlo-based system modeling, which is not possible with RBQ methods. This is another advantage of the proposed method.

Figure 2:
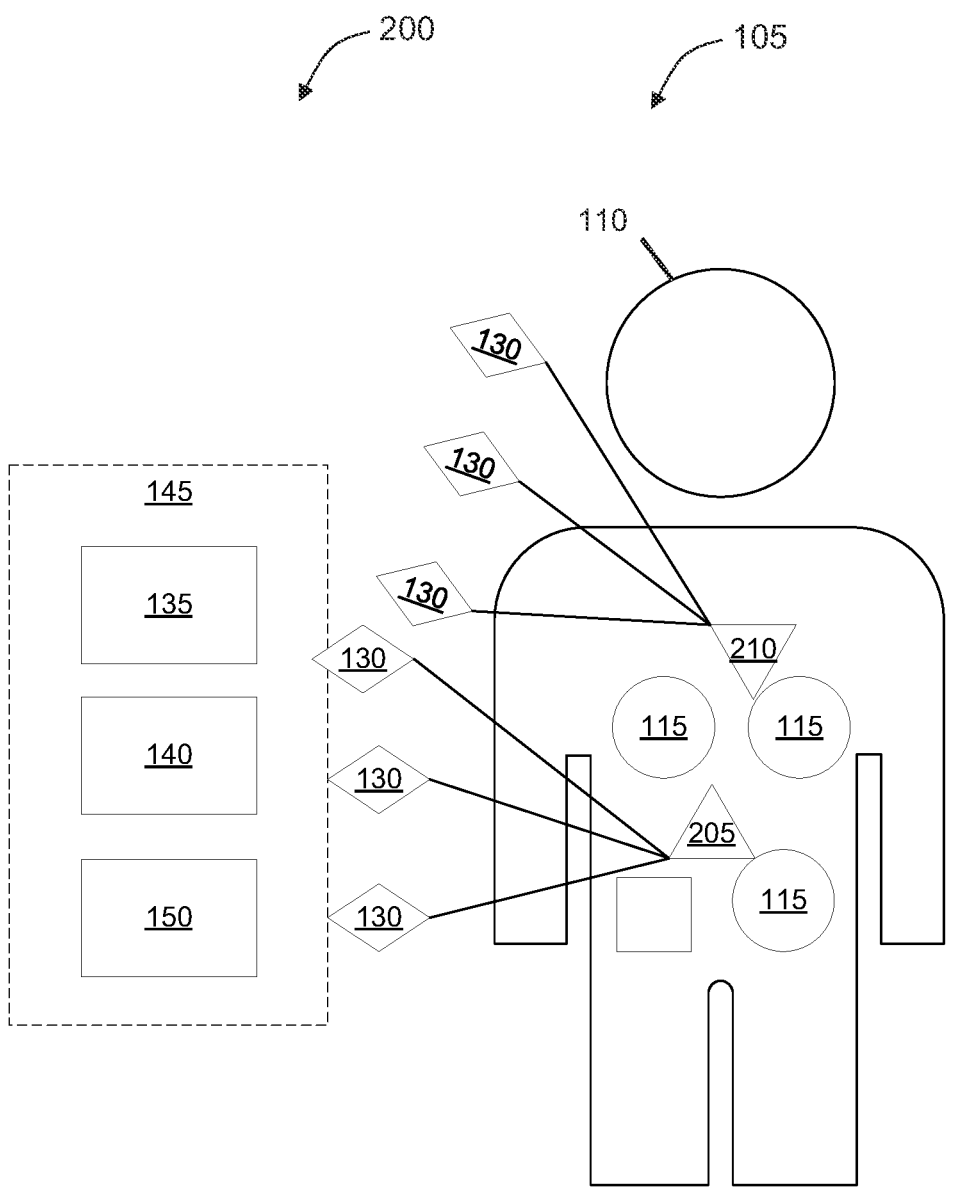
FIG. 2 illustrates a system of performing low-count quantitative SPECT imaging using multiple energy windows in the radiopharmaceutical therapy environment shown in FIG. 1.

FIG. 2 illustrates another system 200 of performing low-count quantitative SPECT imaging using multiple energy windows in the radiopharmaceutical therapy environment 105 (shown in FIG. 1).

The one or more tumors 120 are being treated with an alpha particle-emitting radiopharmaceutical therapy ($\alpha$-RPT) 125 using $^{227}$Th. As described above, the $^{227}$Th $\alpha$-RPT 205 decays into $^{223}$Ra 210. Both the $^{227}$Th 205 and the $^{223}$Ra 210 emit alpha ($\alpha$) particles, which are absorbed by the surrounding tissue, and $\gamma$-ray photons 130, which exit the patient's body. The sensor 135 detects the $\gamma$-ray photons 130. The sensor 135 is a part of a single-photon emission computed tomography (SPECT) system 140. The SPECT system 140 also includes a projection-domain quantification (PDQ) computer system 145 for performing the calculations described herein to detect the location of the $^{227}$Th 205 and the $^{223}$Ra 210 and the based on the detected $\gamma$-ray photons 130.

Thorium-227 ($^{227}$Th) 205 conjugates are an emerging class of radiopharmaceuticals for $\alpha$-particle radiopharmaceutical therapies ($\alpha$-RPTs) 125. Because $^{227}$Th 205 can form stable compounds with chelators that can combine with multiple targeting modalities. $^{227}$Th-based $\alpha$-RPTs 125 have been used in clinical and preclinical studies. The $^{227}$Th 205 emitted $\alpha$-particles that have a short emission range and a high linear energy transfer, thus they can effectively ablate tumors 120 while minimizing damage to surrounding normal tissues. However, since $^{227}$Th 205 and its daughters distribute throughout the body of administered patients, including in radio-sensitive vital organs 115, it is important to manage their absorbed dose. Additionally, dose management also helps adapt treatment regimens, predict therapy outcomes, and monitor adverse events. Dose quantification also helps personalize RPTs.

$^{227}$Th 205 also emits $\gamma$-ray photons 130, which can be detected by a $\gamma$-camera 135. Thus single-photon emission computed tomography (SPECT) can quantify the absorbed dose from the regional activity uptake in organs and lesions in $^{227}$Th-based $\alpha$-RPTs 125. However, this quantification faces several challenges. First, the decay chain of $^{227}$Th 205 is complicated. $^{227}$Th 205 decays to Radium-223 ($^{223}$Ra) 210, another $\alpha$-particle and $\gamma$-ray photon emitter 130, which has a half-life comparable to that of $^{227}$Th 205. $^{223}$Ra 210 can disassociate from the targeting modalities, escape from the original sites of decay, and form an independent biodistribution with $^{227}$Th 205. Consequently, there can be two independently distributed $\alpha$-emitting isotopes within the patient. Second, the $\gamma$-spectra of the two isotopes are highly overlapped, which can lead to crosstalk contamination when imaging them with the SPECT system 140. Last, similar to other $\alpha$-RPTs 125, the administered activity in $^{227}$Th-based $\alpha$-RPT 125 is usually two-to-three orders lower than that in conventional SPECT procedures. Thus, the number of emitted and detected $\gamma$-photons 130 is multiple folds lower than that in conventional SPECT studies.

Current approaches to address crosstalk contamination in dual-isotope quantitative SPECT can be categorized into two groups. The first group is based on pre-reconstruction compensation in the projection domain. A typical such approach is triple energy window (TEW)-based crosstalk compensation, which assumes that crosstalk contamination comes mainly from scattered photons. However, in the joint $^{227}$Th 205 and $^{223}$Ra 210 quantification task, due to the highly overlapped emission spectra, crosstalk contamination is caused by both scattered and primary photons. Thus, TEW-based quantification may be erroneous. In contrast to the pre-reconstruction approaches, another group of approaches jointly reconstruct both isotopes, using an algorithm that incorporates the crosstalk estimation in the iterative process of SPECT image reconstruction. Typical crosstalk estimation methods are based on effective source scatter estimation (ESSE) and Monte Carlo simulations. These methods can be designed to model crosstalk from both primary and scattered photons, and can be used in jointly quantifying $^{227}$Th 205 and $^{223}$Ra 210 activity uptake.

However, even with efficient crosstalk compensation, these approaches are challenged by the low number of detected counts in the application of joint $^{227}$Th 205 and $^{223}$Ra 210 quantification. To account for these issues, the single-isotope low-count quantitative SPECT (LC-QSPECT) method described above for $^{223}$Ra-based $\alpha$-RPTs 125 can be adapted for $^{227}$Th-based $\alpha$-RPTs 125.

The purpose of this adapted LC-QSPECT method is to perform joint quantification of both $^{227}$Th 205 and $^{223}$Ra 210 directly from the projection data. To further address the issue of low counts, both $^{227}$Th 205 and $^{223}$Ra 210 emit gamma-ray photons 130 over multiple photopeak energies. Thus, using photons 130 from multiple energy windows corresponding to these different photopeaks provides a way to improve the effective system sensitivity. Using measurements from multiple energy windows can help improve quantification performance.

Integrating these ideas, a multiple-energy-window projection-domain quantification (MEW-PDQ) method is proposed that jointly estimates the regional activity uptake of $^{227}$Th 205 and $^{223}$Ra 210 directly from low-count SPECT projection data acquired over multiple energy windows.

For the MEW-PDQ method, a SPECT system 140 images a radioisotope distribution of both $^{227}$Th and $^{223}$Ra, denoted as $f^{Th}(r)$ and $f^{Ra}(r)$, respectively, where $r=(x, y, z)$ denote the spatial 3D coordinates. The SPECT system 140 denotes the measured projection data over multiple energy windows and at multiple projection angles by the M-dimensional vector g. The object being imaged and the projection data respectively lie in the Hilbert space of square-integrable functions, denoted by $L_2(R^3)$, and the Hilbert space of Euclidean vectors, is denoted by $E^M$. Then, the SPECT system 140 imaging $^{227}$Th and $^{223}$Ra, denoted by $H^{Th}$ and $H^{Ra}$, respectively, are transformations from $L_2(R^3)$ to $E^M$. In SPECT with α-RPTs, the stray-radiation-related noise forms a substantial portion of the measured counts due to the very low count levels. The SPECT system 140 models this noise as Poisson distributed, with the same mean for all projection bins in the same energy window. But for bins from different energy windows, the means of this noise are different. Let $\Psi$ be an M-dimensional vector that denotes the mean stray-radiation-related noise in the M projection bins. The SPECT system 140 denotes $\Psi_m$ as the $m^{th}$ element of $\Psi$, whose value is determined by the corresponding energy windows it belongs to. The imaging system equation is given by $$g = Hf + \Psi + n \qquad \text{EQ. 1}$$

where $$H = [H^{Th} H^{Ra}], f = \begin{bmatrix} f^{Th} \\ f^{Ra} \end{bmatrix} \qquad \text{EQ. 12}$$

and n is a M-dimensional vector that denotes the entire noise in the imaging system. Then the image data g is Poisson distributed with mean of $Hf+\Psi$. The objective is to estimate the regional uptake of both isotopes within a set of VOIs. Mathematically, a 3D VOI function is defined as:

$$\varphi_k^{VOI}(r) = \begin{cases} 1, & \text{if } r \text{ lies within the } k^{th} \text{ VOI} \\ 0, & \text{otherwise} \end{cases} \qquad \text{EQ. 2}$$

$\lambda^{Th}$ and $\lambda^{Ra}$ denote the K-dimensional vector of regional uptake of $^{227}$Th and $^{223}$Ra, respectively. $\lambda^{Th}$ and $\lambda^{Ra}$ are given by:

$$\lambda_k^{Th} = \frac{\int d^3 r f^{Th}(r) \varphi_k^{VOI}(r)}{\int d^3 r \, \varphi_k^{VOI}(r)} \qquad \text{EQ. 13}$$

and $$\lambda_k^{Ra} = \frac{\int d^3 r f^{Ra}(r) \varphi_k^{VOI}(r)}{\int d^3 r \, \varphi_k^{VOI}(r)} \qquad \text{EQ. 14}$$

In the MEW-PDQ method, the object $^{227}$Th and $^{223}$Ra are represented in terms of the VOI-basis functions as given by EQs. 13 and 14. The activity distributions of $^{227}$Th and $^{223}$Ra are then represented in terms of these basis functions as:

$$f_{VOI}^{Th}(r) = \sum_{k=1}^{K} \lambda_k^{Th} \varphi_k^{VOI}(r) \qquad \text{EQ. 15}$$

and $$f_{VOI}^{Ra}(r) = \sum_{k=1}^{K} \lambda_k^{Ra} \varphi_k^{VOI}(r) \qquad \text{EQ. 15}$$

respectively. If the activity inside of each VOI is constant, then $f^{Th}_{VOI}(r)=f^{Th}(r)$ and $f^{Ra}_{VOI}(r)=f^{Ra}(r)$. Inserting these definitions for f(r) in EQ. 1 yields the following expression for the $m^{th}$ element of vector g:

$$g_m = \int h_m^{Th}(r) f^{Th}(r) d^3 r + \int h_m^{Ra}(r) f^{Ra}(r) d^3 r + \Psi_m + n_m \qquad \text{EQ. 16}$$

$$= \sum_{k=1}^{K} \lambda_k^{Th} \int h_m^{Th}(r) \varphi_k^{VOI}(r) d^3 r +$$

$$\sum_{k=1}^{K} \lambda_k^{Ra} \int h_m^{Ra}(r) \varphi_k^{VOI}(r) d^3 r + \Psi_m + n_m$$

Furthermore, in view of EQ. 12 $H^{Th}$ and $H^{Ra}$ are M×K dimensional system matrices with elements given by:

$$H_{mk}^{Th} = \int d^3 r h_m^{Th}(r) \varphi_k^{VOI}(r) \qquad \text{EQ. 17}$$

and $$H_{mk}^{Ra} = \int d^3 r h_m^{Ra}(r) \varphi_k^{VOI}(r) \qquad \text{EQ. 18}$$

respectively. Given the measured SPECT projection g, to estimate λ, the SPECT system 140 maximizes the probability of occurrence of the measured data. Next the SPECT system 140 denotes Pr(x) as the probability of a discrete random variable x. Then, the probability of the measured projection data is given by:

$$Pr(g|\lambda) = \prod_{m=1}^{M} Pr(g_m|\lambda) \qquad \text{EQ. 8}$$

where the measured data across the different bins and different energy windows are independent. Now, the measured data $g_m$ is Poisson distributed with mean $(H\lambda)_m + \Psi_m$. Thus:

$$Pr(g|\lambda) = \prod_{m=1}^{M} \exp[-1(H\lambda)_m - \Psi_m] \frac{[(H\lambda)_m + \Psi_m]^{g_m}}{g_m!} \qquad \text{EQ. 19}$$

This gives the likelihood of the measured data g. To estimate λ, the SPECT system 140 maximizes the logarithm of the likelihood of λ given g:

$$\hat{\lambda} = \arg_\lambda^{max} \ln[Pr(g|\lambda)] \qquad \text{EQ. 10}$$

To maximize this log-likelihood, the SPECT system 140 follows the same process as used to derive the conventional MLEM technique. The SPECT system 140 differentiates the log-likelihood with respect to the elements of λ and equate that to 0 to find the point at which the log-likelihood is maximized. This yields the following iterative estimates of activity uptake at $^{227}$Th and $^{223}$Ra in the $k^{th}$ VOI, denoted by $\widehat{\lambda_k^{Th}}$ and $\widehat{\lambda_k^{Ra}}$, respectively:

$$\widehat{\lambda_k^{Th}}^{(t+1)} = \widehat{\lambda_k^{Th}}^{(t)} \frac{1}{\sum_{m=1}^{M} H_{mk}^{Th}} \sum_{m=1}^{M} \frac{g_m}{[H\hat{\lambda}^{(t)}]_m + \Psi_m} H_{mk}^{Th}(r) \qquad \text{EQ. 20}$$

-continued $$\lambda_k^{\widehat{Ra}\,(t+1)} = \lambda_k^{\widehat{Ra}\,(t)} \frac{1}{\sum_{m=1}^{M} H_{mk}^{Ra}} \sum_{m=1}^{M} \frac{g_m}{\left[H\lambda^{(t)}\right]_m + \Psi_m} H_{mk}^{Ra} \qquad \text{EQ. 21}$$

where $\lambda_k^{\widehat{Th}}$ and $\lambda_k^{\widehat{Ra}}$, denote the estimate of $\lambda_k^{Th}$ and $\lambda_k^{Ra}$ at the $t^{th}$ iteration, respectively. This procedure is the multiple-energy-window projection-domain quantification (MEW-PDQ) method described herein. This method directly quantifies from projection data by providing the ability to model stray-radiation-related noise and account for cross-talk between $^{227}$Th and $^{223}$Ra. This ability to model stray-radiation-related noise and account for cross-talk plays a key role in the task of reliable quantification.

The proposed MEW-PDQ method also has several advantages. First, the method makes use of projection data from multiple energy windows, which can improve the effective system sensitivity and thus improve on the theoretical precision limits. Second, the number of VOIs. K, is less than the number of voxels that need to be reconstructed in the image reconstruction-based approaches. Next, the method is less sensitive to partial volume effects (PVEs). PVEs are considered as a major degrading effect in image reconstruction-based quantitative SPECT. PVEs include two distinct phenomena: One is due to the finite system resolution, and the other, called tissue-fraction effects, is due to the pixelized representation of a continuous object. The proposed method is less affected by the system resolution since the boundaries of VOIs are defined before estimating the regional uptake. Additionally, the tissue-fraction effects are eliminated since there are no voxelizations. Further, the SPECT system 140 directly estimates the regional uptake from the projection data, thus avoiding any reconstruction-related information loss.

Implementing the proposed MEW-PDQ method requires obtaining the elements of the system matrices of $^{227}$Th and $^{223}$Ra, as shown in EQs. 20 and 21. Some of these elements may be obtained using an MC-based approach. More specifically, the SPECT system 140 can be used to model the isotope emission and the system 200 as a whole. Next, for a given patient, the SPECT system 140 obtains the definition of the VOIs. The VOIs can be obtained, for example, by segmenting the CT that is acquired along with the SPECT information. The SPECT system 140 can assign unit uptake to the VOI and zero uptake elsewhere. In some embodiments, the SPECT system 140 generates an attenuation map of the patient based on historical information, either that from the patient or from other historical patients with similar attributes.

Next, the MEW-PDQ method requires obtaining the mean of stray-radiation-related noise, i.e. $\Psi_m$ in EQs. 20 and 21. This can be obtained experimentally from a planar blank scan acquired on the SPECT system 140 for over 10 minutes. Averaging the projection bin counts in this scan yields the mean background counts. This can then be scaled to the acquisition time to estimate the mean stray-radiation-related noise of each bin corresponding to each energy window. Projection bins surround the subject.

I believe this refers to the fact that in our paper, we use counts in projection bins far away from the object to estimate mean of stray-radiation-related noise. This is because we did not get the chance to measure that in every energy window experimentally. We can remove this sentence or say, for example, "Counts in projection bins far away from the subject can also be used to estimate the mean of stray-radiation-related noise in each energy window."

The computed system matrix and mean stray-radiation-related noise are used in EQs. 20 and 21 to estimate the regional uptake directly from the projection data. As the system matrix modeled all relevant image-degrading processes, these processes were automatically compensated during quantification.

One important feature of the MEW-PDQ method is the use of multiple energy windows in quantification. Using multiple energy windows can reduce the lower bound of the variance that can be achieved by the proposed method and thus may improve its precision. Quantifying uptake precisely is a major challenge, especially when the number of counts is low; however, the MEW-PDQ method accounts for that issue.

Another important feature of the MEW-PDQ method is the use of an MC simulation-based approach to generate the system matrix. This approach yields highly accurate modeling of SPECT physics. The MC approach is computationally feasible because the number of VOIs is typically quite small. Thus, this matrix can be pre-computed and stored. In clinical applications, the CT scans of the patient are acquired first, then the system matrix can be generated simultaneously when the SPECT scan is acquired. Further, the estimation process is rapid. This is unlike developing such an approach for OSEM-based methods, for which a similar system matrix may require up to 30 TB of memory. Thus, the proposed method provides a mechanism for highly accurate Monte Carlo-based system modeling, which is not possible with RBQ methods. This is another advantage of the proposed method.

In the exemplary embodiments, the LC-QSPECT method and the MEW-PDQ method can be used to identify the locations of α-RPTs 125 in a patient 110. Furthermore, the PDQ computer device 145 can also store a plurality of historical information of patients 110 and locations of α-RPTs 125 in those patients 110. The PDQ computer device 145 can use the historical information to generate one or more models of behavior of patients 110 with different attributes, such as, but not limited to, weight, age, height, tumor or lesion size, tumor or lesion locations, α-RPT 125 dosage size, α-RPT 125 dosage location, and other attributes. The PDQ computer device 145 can provide those models to assist in planning the treatments of future patients 110. For example, the model may determine based on historical information where different α-RPT 125 dosages may travel based on the different attributes. This may assist in determining optimal positioning of α-RPT 125 dosages to ensure that the significant portion of the dosages are applied to the tumor 120 and not to the organs 115. Furthermore, the PDQ computer device 145 may model how the $^{227}$Th 205 decays in the body and where the $^{223}$Ra 210 may appear based on the application and location of the $^{227}$Th 205. The PDQ computer device 145 may apply machine learning techniques to model the patient 110 based on the historical information.

In other embodiments, the PDQ computer device 145 may model the configuration of one or more sensors 135 and other devices in the SPECT system 140. The PDQ computer device 145 may determine differences in how each device reacts and is calibrated based on its configuration to assist with modeling the location information and the LC-QSPECT and MEW-PDQ methods.

Figure 3:
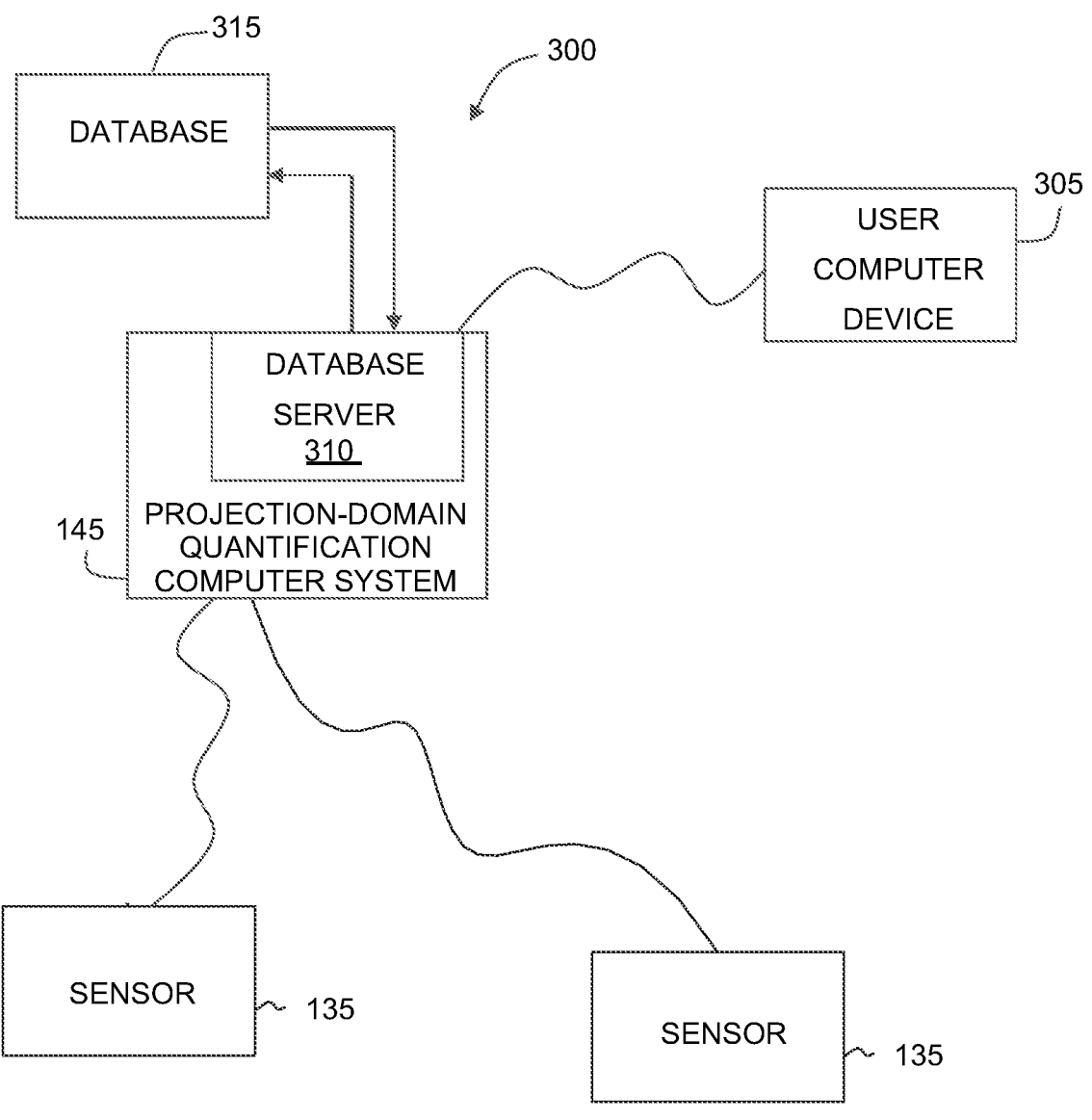
FIG. 3 illustrates a computer system for performing low-count quantitative SPECT imaging in the system and environment shown in FIG. 1.

FIG. 3 illustrates a simplified block diagram of an exemplary computer system 300 for implementing the LC-QSPECT method and the MEW-PDQ method described in FIGS. 1 and 2. In the exemplary embodiment, computer system 300 may be used for determining the location of α-RPTs 125 in a patient 110 (shown in FIG. 1). As described below in more detail, a PDQ computer device 145 (also known as a PDQ server 145) may be configured to i) store a computer tomography (CT) scan of a subject being examining including a plurality of defined volumes of interest (VOIs) of the subject being examined; ii) model a system matrix based on the stored CT scan, wherein the model describes the probability that photons emitted from each of the defined VOIs are detected in different projection bins, where a plurality of projection bins are defined around the subject and the defined VOIs; iii) adjust the model with analysis of stray-radiation noise around the subject; iv) detect, by the one or more sensors, one or more photons being emitted by an alpha-particle-emitting isotope within the subject; and v) execute the adjusted model with the one or more detected photons as inputs to determine a source VOI of the detected photons.

In the exemplary embodiment, user computer devices 305 are computers that include a web browser or a software application, which enables user computer devices 305 to access remote computer devices, such as the PDQ computer device 145, using the Internet or other network. More specifically, user computer devices 305 may be communicatively coupled to the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular phone connection, and a cable modem. User computer devices 305 may be any device capable of accessing the Internet including, but not limited to, a desktop computer, a laptop computer, a personal digital assistant (PDA), a cellular phone, a smartphone, a tablet, a phablet, wearable electronics, smart watch, or other web-based connectable equipment or mobile devices.

A database server 310 may be communicatively coupled to a database 315 that stores data. In one embodiment, database 315 may include SPECT projection data, VOI activity data, and system model data. Non-limiting examples of suitable VOI activity data include a plurality of values representative of activity within each VOI obtained using the disclosed method. In one aspect, the system model data includes any values defining the parameters of the model representing the physics of obtaining projection data using the SPECT system 145. In one aspect, the SPECT projection data includes any values of signals indicative of projection data obtained using the SPECT imaging system 145. In the exemplary embodiment, database 315 may be stored remotely from the PDQ computer device 145. In some embodiments, database 315 may be decentralized. In the exemplary embodiment, the user may access database 315 via user computer device 305 by logging onto PDQ computer device 145, as described herein.

PDQ computer device 145 may be communicatively coupled with one or more sensors 135 and user computer device 305. In some embodiments, PDQ computer device 145 may be associated with, or is part of a computer network associated with a SPECT system 140 or individual scanner. In other embodiments, PDQ computer device 145 may be associated with a third party and is merely in communication with the SPECT system 140. More specifically, the PDQ computer device 145 is communicatively coupled to the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular phone connection, and a cable modem. The PDQ computer device 145 may be any device capable of accessing the Internet including, but not limited to, a desktop computer, a laptop computer, a personal digital assistant (PDA), a cellular phone, a smartphone, a tablet, a phablet, wearable electronics, smart watch, or other web-based connectable equipment or mobile devices. In the exemplary embodiment, the PDQ computer device 145 hosts an application or website that allows the user to perform analysis of SPECT imaging in line with the LC-QSPECT method and/or the MEW-PDQ method.

Figure 4:
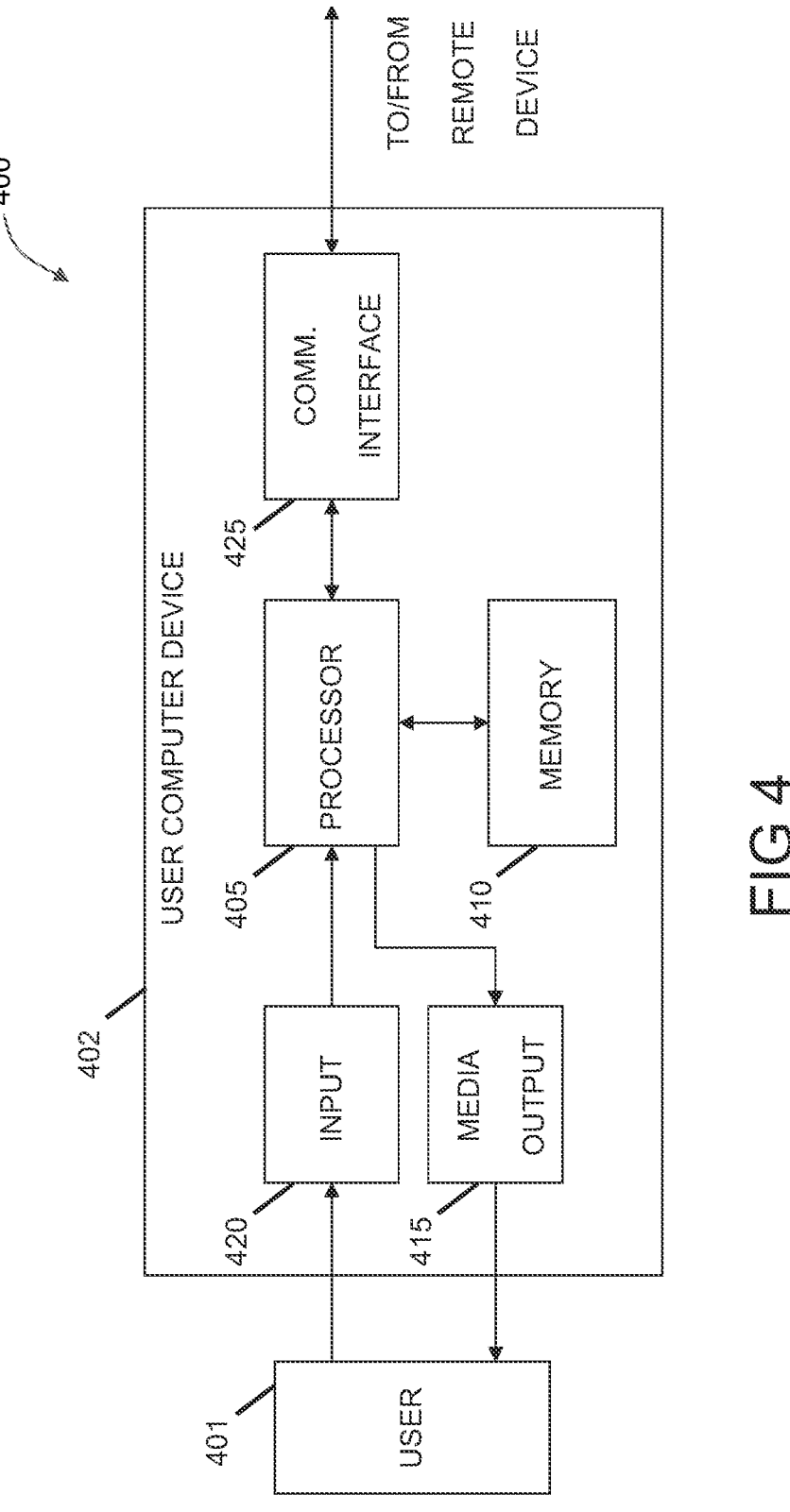
FIG. 4 illustrates an example configuration of a client system shown in FIG. 3, in accordance with one embodiment of the present disclosure.

FIG. 4 depicts an exemplary configuration of the computer devices shown in FIG. 1, in accordance with one embodiment of the present disclosure. User computer device 402 may be operated by a user 401. User computer device 402 may include, but is not limited to, PDQ computer device 145 (shown in FIG. 1) and user computer device 305 (shown in FIG. 3). User computer device 402 may include a processor 405 for executing instructions. In some embodiments, executable instructions are stored in a memory area 410. Processor 405 may include one or more processing units (e.g., in a multi-core configuration). Memory area 410 may be any device allowing information such as executable instructions and/or transaction data to be stored and retrieved. Memory area 410 may include one or more computer readable media.

User computer device 402 may also include at least one media output component 415 for presenting information to user 401. Media output component 415 may be any component capable of conveying information to user 401. In some embodiments, media output component 415 may include an output adapter (not shown) such as a video adapter and/or an audio adapter. An output adapter may be operatively coupled to processor 405 and operatively coupleable to an output device such as a display device (e.g., a cathode ray tube (CRT), liquid crystal display (LCD), light emitting diode (LED) display, or "electronic ink" display) or an audio output device (e.g., a speaker or headphones).

In some embodiments, media output component 415 may be configured to present a graphical user interface (e.g., a web browser and/or a client application) to user 401. A graphical user interface may include, for example, analysis of α-RPT 125 (shown in FIG. 1) locations. In some embodiments, user computer device 402 may include an input device 420 for receiving input from user 401. User 401 may use input device 420 to, without limitation, select and/or enter one or more α-RPTs 125.

Input device 420 may include, for example, a keyboard, a pointing device, a mouse, a stylus, a touch sensitive panel (e.g., a touch pad or a touch screen), a gyroscope, an accelerometer, a position detector, a biometric input device, and/or an audio input device. A single component such as a touch screen may function as both an output device of media output component 415 and input device 420.

User computer device 402 may also include a communication interface 425, communicatively coupled to a remote device such as PDQ computer device 145 or sensor 135. Communication interface 425 may include, for example, a wired or wireless network adapter and/or a wireless data transceiver for use with a mobile telecommunications network.

Stored in memory area 410 are, for example, computer readable instructions for providing a user interface to user 401 via media output component 415 and, optionally, receiving and processing input from input device 420. A user interface may include, among other possibilities, a web browser and/or a client application. Web browsers enable users, such as user 401, to display and interact with media and other information typically embedded on a web page or a website from vehicle controller 110. A client application allows user 401 to interact with, for example, sensors 135. For example, instructions may be stored by a cloud service, and the output of the execution of the instructions sent to the media output component 415.

Processor 405 executes computer-executable instructions for implementing aspects of the disclosure. In some embodiments, the processor 405 is transformed into a special purpose microprocessor by executing computer-executable instructions or by otherwise being programmed. For example, the processor 405 may be programmed with the instructions such as the LC-QSPECT method and the MEW-PDQ method.

In some embodiments, user computer device 402 may include, or be in communication with, one or more sensors, such as sensor 135 (shown in FIG. 1). User computer device 402 may be configured to receive data from the one or more sensors and store the received data in memory area 410. Furthermore, user computer device 402 may be configured to transmit the sensor data to a remote computer device, such as PDQ computer device 145, through communication interface 425.

Figure 5:
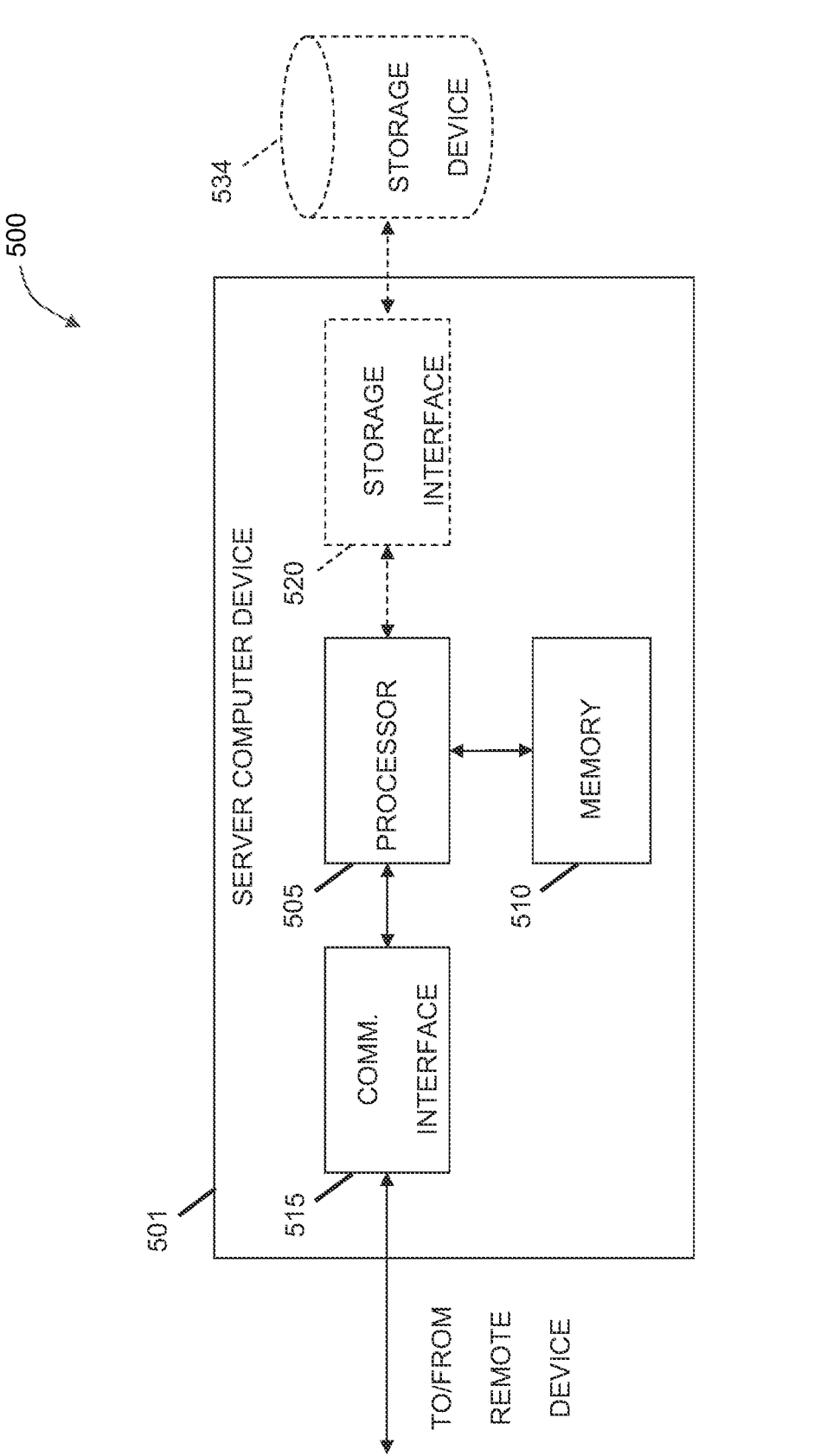
FIG. 5 illustrates an example configuration of a server system shown in FIG. 4, in accordance with one embodiment of the present disclosure.

FIG. 5 illustrates an example configuration of the server system shown in FIG. 3, in accordance with one embodiment of the present disclosure. Server computer device 501 may include, but is not limited to, PDQ computer device 145 (shown in FIG. 1) and database server 315 (shown in FIG. 3). Server computer device 501 also includes a processor 505 for executing instructions. Instructions may be stored in a memory area 510. Processor 505 may include one or more processing units (e.g., in a multi-core configuration).

Processor 505 is operatively coupled to a communication interface 515 such that server computer device 501 is capable of communicating with a remote device such as another server computer device 501, PDQ computer device 145, sensors 135, or user computer device 305 (shown in FIG. 3). For example, communication interface 515 may receive requests from user computer devices 305 and information from sensors 135 (shown in FIG. 1) via the Internet, as illustrated in FIG. 3.

Processor 505 may also be operatively coupled to a storage device 534. Storage device 534 is any computer-operated hardware suitable for storing and/or retrieving data, such as, but not limited to, data associated with database 315 (shown in FIG. 3). In some embodiments, storage device 534 is integrated in server computer device 501. For example, server computer device 501 may include one or more hard disk drives as storage device 534. In other embodiments, storage device 534 is external to server computer device 501 and may be accessed by a plurality of server computer devices 501. For example, storage device 534 may include a storage area network (SAN), a network attached storage (NAS) system, and/or multiple storage units such as hard disks and/or solid state disks in a redundant array of inexpensive disks (RAID) configuration.

In some embodiments, processor 505 is operatively coupled to storage device 534 via a storage interface 520. Storage interface 520 is any component capable of providing processor 505 with access to storage device 534. Storage interface 520 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 505 with access to storage device 534.

Processor 505 executes computer-executable instructions for implementing aspects of the disclosure. In some embodiments, the processor 505 is transformed into a special purpose microprocessor by executing computer-executable instructions or by otherwise being programmed. For example, the processor 505 is programmed with instructions such as illustrated in the LC-QSPECT method and the MEW-PDQ method.

The computer-implemented methods and processes described herein may include additional, fewer, or alternate actions, including those discussed elsewhere herein. The present systems and methods may be implemented using one or more local or remote processors, transceivers, and/or sensors (such as processors, transceivers, and/or sensors mounted on computer systems or mobile devices, or associated with or remote servers), and/or through implementation of computer-executable instructions stored on non-transitory computer-readable media or medium. Unless described herein to the contrary, the various steps of the several processes may be performed in a different order, or simultaneously in some instances.

Additionally, the computer systems discussed herein may include additional, fewer, or alternative elements and respective functionalities, including those discussed elsewhere herein, which themselves may include or be implemented according to computer-executable instructions stored on non-transitory computer-readable media or medium.

In the exemplary embodiment, a processing element may be instructed to execute one or more of the processes and subprocesses described above by providing the processing element with computer-executable instructions to perform such steps/sub-steps, and store collected data (e.g., vehicle profiles, etc.) in a memory or storage associated therewith. This stored information may be used by the respective processing elements to make the determinations necessary to perform other relevant processing steps, as described above.

The aspects described herein may be implemented as part of one or more computer components, such as a client device, system, and/or components thereof, for example. Furthermore, one or more of the aspects described herein may be implemented as part of a computer network architecture and/or a cognitive computing architecture that facilitates communications between various other devices and/or components. Thus, the aspects described herein address and solve issues of a technical nature that are necessarily rooted in computer technology.

A processor or a processing element may be trained using supervised or unsupervised machine learning, and the machine learning program may employ a neural network, which may be a convolutional neural network, a deep learning neural network, a reinforced or reinforcement learning module or program, or a combined learning module or program that learns in two or more fields or areas of interest. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as images, object statistics and information, traffic timing, previous trips, and/or actual timing. The machine learning programs may utilize deep learning algorithms that may be primarily focused on pattern recognition, and may be trained after processing multiple examples. The machine learning programs may include Bayesian Program Learning (BPL), voice recognition and synthesis, image or object recognition, optical character recognition, and/or natural language processing-either individually or in combination. The machine learning programs may also include natural language processing, semantic analysis, automatic reasoning, and/or machine learning.

Supervised and unsupervised machine learning techniques may be used. In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs. In one embodiment, machine learning techniques may be used to determine where treatments may migrate to within the body.

Based upon these analyses, the processing element may learn how to identify characteristics and patterns that may then be applied to analyzing image data, model data, and/or other data. For example, the processing element may learn, to identify trends of locations based on photon vectors and locations. The processing element may also learn how to identify trends that may not be readily apparent based upon collected data, such as trends that identifying optimal placement of treatments in the body relative to tumors.

The singular forms "a," "an," and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

As used herein, the term "database" may refer to either a body of data, a relational database management system (RDBMS), or to both, and may include a collection of data including hierarchical databases, relational databases, flat file databases, object-relational databases, object oriented databases, and/or another structured collection of records or data that is stored in a computer system. The above examples are not intended to limit in any way the definition and/or meaning of the term database. Examples of RDBMS's include, but are not limited to, Oracle® Database, MySQL, IBM® DB2, Microsoft® SQL Server, Sybase®, and PostgreSQL. However, any database may be used that enables the systems and methods described herein. (Oracle is a registered trademark of Oracle Corporation, Redwood Shores, California; IBM is a registered trademark of International Business Machines Corporation, Armonk, New York; Microsoft is a registered trademark of Microsoft Corporation, Redmond, Washington; and Sybase is a registered trademark of Sybase, Dublin, California.)

A computer program of one embodiment is embodied on a computer-readable medium. In an example, the system is executed on a single computer system, without requiring a connection to a server computer. In a further example embodiment, the system is being run in a Windows® environment (Windows is a registered trademark of Microsoft Corporation, Redmond, Washington). In yet another embodiment, the system is run on a mainframe environment and a UNIX® server environment (UNIX is a registered trademark of X/Open Company Limited located in Reading, Berkshire, United Kingdom). In a further embodiment, the system is run on an iOS® environment (iOS is a registered trademark of Cisco Systems, Inc. located in San Jose, CA). In yet a further embodiment, the system is run on a Mac OS® environment (Mac OS is a registered trademark of Apple Inc. located in Cupertino, CA). In still yet a further embodiment, the system is run on Android® OS (Android is a registered trademark of Google, Inc. of Mountain View, CA). In another embodiment, the system is run on Linux® OS (Linux is a registered trademark of Linus Torvalds of Boston, MA). The application is flexible and designed to run in various different environments without compromising any major functionality. In some embodiments, the system includes multiple components distributed among a plurality of computing devices. One or more components are in the form of computer-executable instructions embodied in a computer-readable medium. The systems and processes are not limited to the specific embodiments described herein. In addition, components of each system and each process can be practiced independently and separately from other components and processes described herein. Each component and process can also be used in combination with other assembly packages and processes As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit (ASIC), and other programmable circuits, and these terms are used interchangeably herein. In the embodiments described herein, memory may include, but is not limited to, a computer-readable medium, such as a random-access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable and include any computer program storage in memory for execution by personal computers, workstations, clients, servers, and respective processing elements thereof.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device, and a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Furthermore, as used herein, the term "real-time" refers to at least one of the time of occurrence of the associated events, the time of measurement and collection of predetermined data, the time for a computing device (e.g., a processor) to process the data, and the time of a system response to the events and the environment. In the embodiments described herein, these activities and events may be considered to occur substantially instantaneously.

Exemplary embodiments of systems and methods for securely navigating traffic lights are described above in detail. The systems and methods of this disclosure though, are not limited to only the specific embodiments described herein, but rather, the components and/or steps of their implementation may be utilized independently and separately from other components and/or steps described herein.

Although specific features of various embodiments may be shown in some drawings and not in others, this is for convenience only. In accordance with the principles of the systems and methods described herein, any feature of a drawing may be referenced or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a programmable logic unit (PLU), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

The patent claims at the end of this document are not intended to be construed under 35 U.S.C. § 112(f) unless traditional means-plus-function language is expressly recited, such as "means for" or "step for" language being expressly recited in the claim(s).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for low-count quantitative single-photon emission computed tomography (LC-QSPECT) comprising:
   one or more sensors configured for detecting one or more emitted photons; and
   a computer device in communication with the one or more sensors, wherein the computer device comprises at least one processor in communication with at least one memory device, wherein the at least one processor is programmed to:
   store a computer tomography (CT) scan of a subject being examining including a plurality of defined volumes of interest (VOIs) of the subject being examined;
   define the plurality of defined VOIs based on the CT scan of the subject being examined, wherein the plurality of defined VOIs are different than and have different boundaries from any plurality of voxels defining the subject to be examined;
   model a system matrix based on the stored CT scan, wherein the model describes the probability that photons emitted from each of the plurality of defined VOIs are detected in different projection bins, wherein a plurality of projection bins are defined around the subject and the plurality of defined VOIs;
   adjust the model with analysis of stray-radiation noise around the subject;
   detect, by the one or more sensors, one or more photons being emitted by an alpha-particle-emitting isotope within the subject; and
   execute the adjusted model with the one or more detected photons as inputs to determine a source VOI of the one or more detected photons.

2. The system in accordance with claim 1, wherein the at least one processor is further programmed to determine an uptake amount within one or more regions of the subject based on the source VOI.

3. The system of claim 1, wherein the alpha-particle-emitting isotope is a part of a radiopharmaceutical therapy for treating the subject.

4. The system of claim 3, wherein subject has one or more tumors and are being treated with the alpha-particle-emitting isotope.

5. The system of claim 1, wherein the at least one processor is further programmed to store of model of stray-radiation-related noise.

6. The system of claim 5, wherein the at least one processor is further programmed to obtain a mean of stray-radiation-related noise.

7. The system of claim 6, wherein the at least one processor is further programmed to:
   receive a blank scan from the one or more sensors for a period of time; and
   determine the mean of stray-radiation-related noise based on scaling of the blank scan.

8. The system of claim 1, wherein the model simulates the physics of the absorption by the subject and SPECT physics, and wherein the model simulates relevant image degrading processes.

9. The system of claim 8, wherein the at least one processor is further programmed to generate the model using Monte Carlo simulations of the SPECT physics.

10. The system of claim 1, wherein the at least one processor is further programmed to:

receive a CT scan of the subject; and determine a plurality of VOIs in the subject based on segmenting the CT scan.

11. The system of claim 10, wherein the at least one processor is further programmed to assign unit uptake to the VOIs and zero elsewhere for the model.

12. The system of claim 1, wherein the at least one processor is further programmed to:

receive historical information; and generate an attenuation map of the subject based on the historical information and the received CT scan.

13. The system of claim 12, wherein the historical information is from the subject itself.

14. The system of claim 12, wherein the historical information is from other subjects with similar attributes to the subject.

15. The system of claim 1, wherein the at least one processor is further programmed to detect activity uptake in one or more regions of the subject, wherein there are two alpha-particle-emitting isotopes within the subject.

16. The system of claim 15, wherein a first alpha-particle-emitting isotope within the subject is 227Th and wherein a second alpha-particle-emitting isotope is 223Ra.

17. The system of claim 16, wherein the first alpha-particle-emitting isotope decayed into the second alpha-particle-emitting isotope.

18. The system of claim 15, wherein the model accounts for cross-talk between radionuclides in multiple different energy windows.

19. A method for low-count quantitative single-photon emission computed tomography (LC-QSPECT), the method implemented by a computer device comprising at least one processor in communication with one or more memory devices and in communication with one or more sensors configured for detecting one or more emitted photons, the method comprises:

storing a computer tomography (CT) scan of a subject being examining including a plurality of defined volumes of interest (VOIs) of the subject being examined;

defining the plurality of defined VOIs based on the CT scan of the subject being examined, wherein the plurality of defined VOIs are different than and have different boundaries from any plurality of voxels defining the subject to be examined;

modeling a system matrix based on the stored CT scan, wherein the model describes the probability that photons emitted from each of the plurality of defined VOIs are detected in different projection bins, wherein a plurality of projection bins are defined around the subject and the plurality of defined VOIs;

adjusting the model with analysis of stray-radiation noise around the subject;

detecting, by the one or more sensors, one or more photons being emitted by an alpha-particle-emitting isotope within the subject; and executing the adjusted model with the one or more detected photons as inputs to determine a source VOI of the one or more detected photons.

20. A computer device for low-count quantitative single-photon emission computed tomography (LC-QSPECT) comprising at least one processor in communication with at least one memory device, wherein the at least one processor is programmed to:

store a computer tomography (CT) scan of a subject being examining including a plurality of defined volumes of interest (VOIs) of the subject being examined;

define the plurality of defined VOIs based on the CT scan of the subject being examined, wherein the plurality of defined VOIs are different than and have different boundaries from any plurality of voxels defining the subject to be examined;

model a system matrix based on the stored CT scan, wherein the model describes the probability that photons emitted from each of the plurality of defined VOIs are detected in different projection bins, wherein a plurality of projection bins are defined around the subject and the plurality of defined VOIs;

adjust the model with analysis of stray-radiation noise around the subject;

detect, by one or more sensors, one or more photons being emitted by an alpha-particle-emitting isotope within the subject; and execute the adjusted model with the one or more detected photons as inputs to determine a source VOI of the one or more detected photons.

* * * * *